United States Patent
Reynolds

(10) Patent No.: US 6,857,133 B2
(45) Date of Patent: Feb. 22, 2005

(54) METHOD AND APPARATUS FOR MANUFACTURING AND INSTALLING WATER RESISTANT COVER ON A LIMB

(76) Inventor: David V. Reynolds, 3220 W. Echo La., Phoenix, AZ (US) 85051

( * ) Notice: Subject to any disclaimer, the term of this patent is extended or adjusted under 35 U.S.C. 154(b) by 268 days.

(21) Appl. No.: 10/141,259

(22) Filed: May 7, 2002

(65) Prior Publication Data
US 2003/0208827 A1 Nov. 13, 2003

(51) Int. Cl.[7] ............................................. A41D 13/00
(52) U.S. Cl. ........................................... 2/16; 602/62
(58) Field of Search ............................... 2/16, 59, 125, 2/126, 22, 23, 17, 161.5, 69, 69.5, 170, 309–313, 161.1, 158, 159; 128/82; 602/62, 63; 24/122 B, 129 D, 712.7, 115 H, 66.9, 30.5 S

(56) References Cited

U.S. PATENT DOCUMENTS

| | | | | |
|---|---|---|---|---|
| 3,820,200 A | * | 6/1974 | Myers | 24/30.5 S |
| 4,570,304 A | * | 2/1986 | Montreuil et al. | 24/30.5 S |
| 4,639,945 A | * | 2/1987 | Betz | 2/22 |
| 5,063,919 A | * | 11/1991 | Silverberg | 602/3 |
| 5,195,218 A | * | 3/1993 | Joseph et al. | 24/129 R |
| 5,699,632 A | * | 12/1997 | Stout et al. | 43/25 |
| 6,237,252 B1 | * | 5/2001 | Cook | 36/50.1 |
| 6,421,830 B1 | * | 7/2002 | Reynolds | 2/59 |

* cited by examiner

Primary Examiner—Gloria M. Hale
(74) Attorney, Agent, or Firm—Tod R. Nissle, P.C.

(57) ABSTRACT

A water resistant covering covers a part of the body, prevents water from penetrating the covering, and can be emplaced on the body with a single hand.

6 Claims, 4 Drawing Sheets

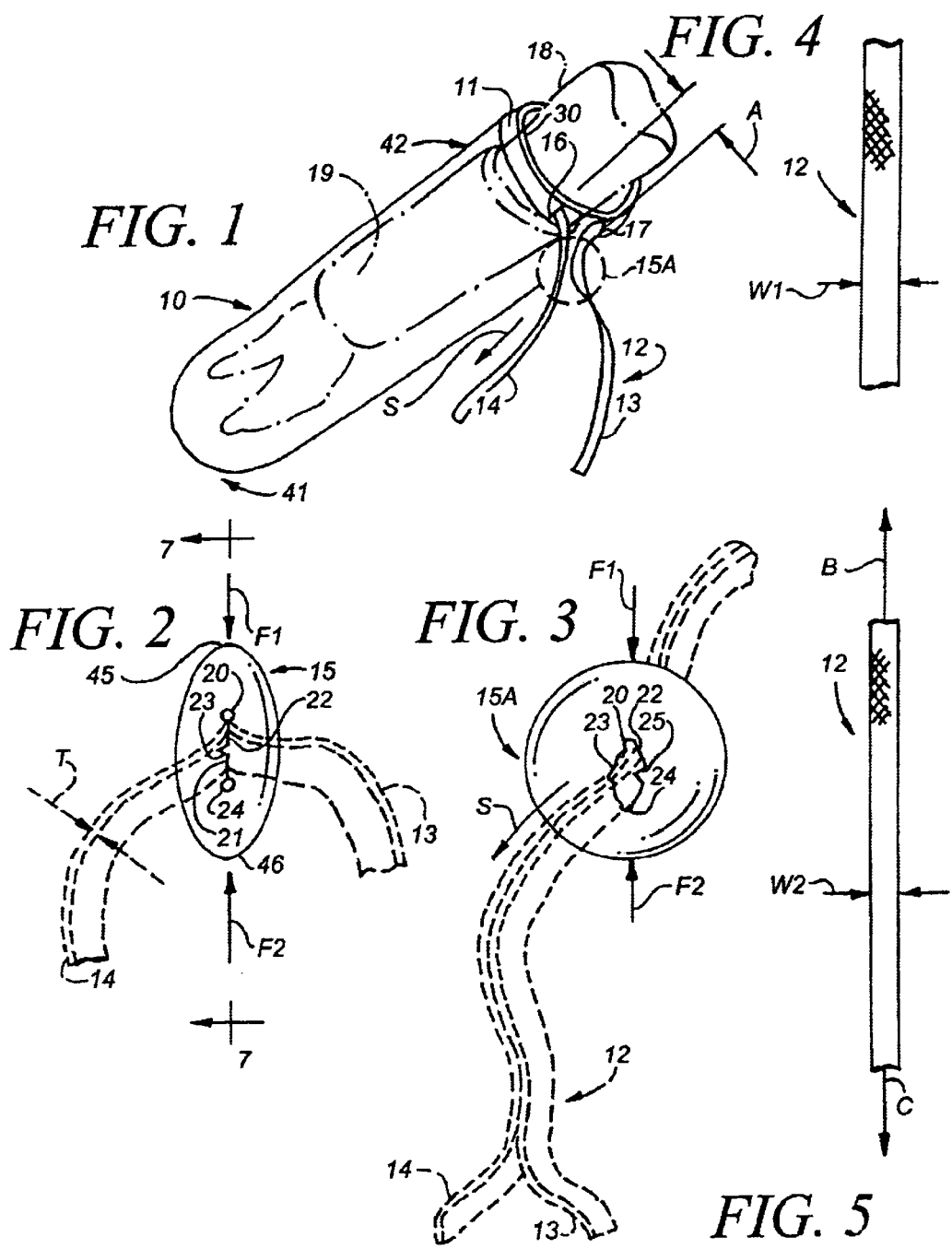

FIG. 8
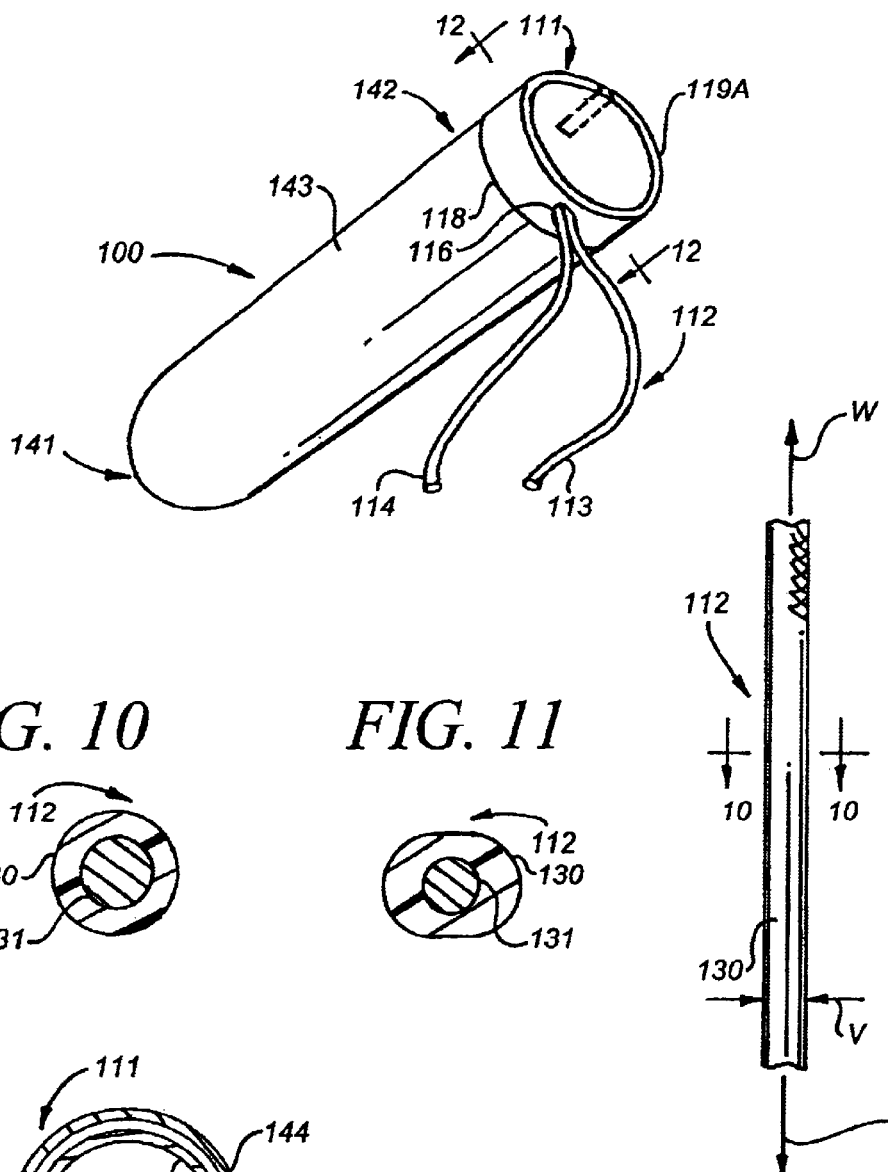
FIG. 10
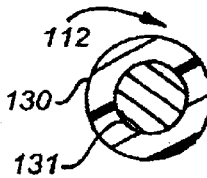
FIG. 11
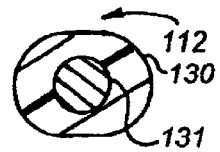
FIG. 12
FIG. 9

METHOD AND APPARATUS FOR MANUFACTURING AND INSTALLING WATER RESISTANT COVER ON A LIMB

This invention pertains to water resistant coverings.

More particularly, the invention pertains to a water resistant covering which is installed on an arm, leg, or other extremity or part of the body to cover a cast or otherwise protect the body and to prevent water from penetrating the covering.

In a further respect, the invention pertains to a method for enabling an individual to use only a single hand to conveniently put a water resistant covering on an arm or leg.

Water resistant coverings for the arm or leg are well known in the art. See, for example, U.S. Pat. No. 6,047,403 to Juozaitis, U.S. Pat. No. 5,761,746 to Brown, U.S. Pat. No. 5,342,286 to Kelly et al., U.S. Pat. No. 5,542,121 to Lahaussois et al., U.S. Pat. No. 5,728,052 to Meehan, D406,897 to Agati et al., U.S. Pat. No. 4,768,501 to George, U.S. Pat. No. 5,817,038 to Orange et al., U.S. Pat. No. 5,063,919 to Silverberg, U.S. Pat. No. 4,986,265 to Caponi, U.S. Pat. No. 5,720,712 to Joy et al., U.S. Pat. No. 4,523,586 to Couri, U.S. Pat. No. 5,720,713 to Hutchison, and U.S. Pat. No. 5,865,772 to George.

Conventional water resistant coverings are fastened or mounted on the arm or other extremity of an individual using elastic straps, VELCRO(TM) hook and loop fasteners, and other fastening means. Such prior art fastening systems, while functioning to maintain the covering in place on the user's extremity, appear to suffer from certain disadvantages. First, some fastening systems tend to restrict blood circulation in and movement of the user's extremity. Second, other fastening systems are not readily quickly removed from the user's extremity. Third, still other prior art systems are not readily installed without the help of a second individual. Fourth, yet other prior art systems are comfortable to wear but are not adjustable to insure that they efficiently seal and prevent water from seeping under the water resistant covering.

Accordingly, it would be highly desirable to provide an improved water resistant covering which could be readily installed and removed, which would be comfortable to wear and still prevent water from seeping into the covering, and which would not unnecessarily restrict movement of or blood flow in a user's body.

Therefore, it is a principal object of the instant invention to provide an improved method and apparatus for installing and using a water resistant covering on a part of the body.

Another object of the invention is to provide an improved water resistant covering which can with the use of only a single hand be installed on, removed from, and adjusted on a user's body.

A further object of the invention is to provide a water resistant covering which includes a sealing mechanism that is readily adjusted, efficiently seals, and expands and contracts with tissues in a user's body during movement of the body.

The foregoing and other, further and more specific objects and advantages of the invention will be apparent from the following detailed description of the invention, taken in conjunction with the drawings, in which:

FIG. 1 is a perspective view illustrating a water resistant covering constructed in accordance with the principles of the invention;

FIG. 2 is a front view illustrating a frictional releasable engagement device used in the sealing system of the invention;

FIG. 3 is a front view further illustrating the mode of operation of the frictional releasable engagement device of FIG. 2;

FIG. 4 is a front view illustrating an unstreched flat elastic strip utilized in the sealing system of the invention;

FIG. 5 is a front view illustrating the elastic strip of FIG. 5 after it has been tensioned and stretched by pulling the strip in the opposing directions indicated by arrows B and C;

FIG. 8 is a perspective view illustrating an alternate embodiment of the water resistant covering of the invention;

FIG. 9 is a front view illustrating a draw string utilized in the water resistant covering of FIG. 8;

FIG. 10 is a cross-section view of the draw string of FIG. 9 illustrating additional construction details thereof and taken along section line 10—10;

FIG. 11 is a cross-section view of the draw string of FIG. 9 illustrating the string after it has been elastically distended and taken along section line 10—10;

FIG. 12 is a cross-section view of the hem of the water resistant covering of FIG. 8 illustrating further construction details thereof and taken along section line 12—12 thereof;

Figure 6:
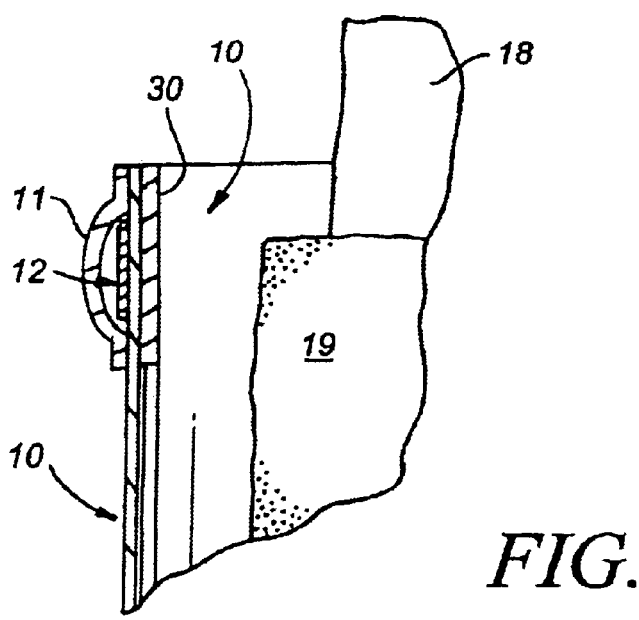
FIG. 6 is a partial sectional view illustrating the water resistant covering of FIG. 1.

Briefly, in accordance with the invention, improvements as provided in combination with a water-resistant sleeve. The sleeve is shaped and dimensioned to fit over a portion of the body of a user and has a distal end and a proximate end. The improvements enable the proximate end of the sleeve to be sealingly secured with a single hand around the portion of the user's body. The improvements include a pliable hem connected to the proximate end of the sleeve and foldable in accordion fashion when drawn closed to fit sealingly around the portion of the user's body; an elongate, elastic flat strip extending through the hem to draw closed sealingly the hem means against the portion of the user's body; and, a releasable engagement system which is operable with a single hand. The engagement system can be operated with a single hand to permit the flat strip to be drawn through the engaging means, to slide the engagement system along the flat strip to a position adjacent the portion of the user's body, and to lock a portion of the flat strip in the engagement system to prevent the strip from sliding through the engagement system.

In another embodiment of the invention, an improved method is provided to sealingly mount a pliable, water-resistant sleeve on a portion of a user's body. The sleeve is shaped and dimensioned to fit over the portion of the user's body. The sleeve includes a distal end and a proximate end; a pliable hem connected to the proximate end of the sleeve and foldable in accordion fashion when drawn closed to fit sealingly around the portion of the user's body; an elongate, elastic flat strip extending through said hem to draw closed sealingly the hem against the portion of the user's body; and, a releasable engagement system. The releasable engagement system is operable with a single hand to permit the flat strip to be drawn through the engagement system, to slide the engagement system along the flat strip to a position adjacent the portion of the user's body, and to lock a portion of the flat strip in the engagement system to prevent the strip from sliding through the engagement system. The improved method includes the steps of mounting the sleeve on the portion of the user's body; and, operating with a single hand the engagement means to draw the flat strip through the engagement system, slide the engagement means along the flat strip to a position adjacent the portion of the user's body, and lock a portion of the flat strip in the engagement system to prevent the strip from sliding through the engagement system.

In a further embodiment of the invention, improvements are provided in combination with a water-resistant sleeve shaped and dimensioned to fit over a portion of the body of a user. The sleeve has a distal end and a proximate end. The portion of the user's body includes tissue which expands and contracts during movement of the extremity. The improvements enable the proximate end of the sleeve to be sealingly secured around with a single hand to the portion of the user's body such that the proximate end when sealingly secured expands and contract simultaneously with expansion and contraction of the portion of the user's body during movement of the portion of the user's body. The improvements include a pliable hem connected to the proximate end of the sleeve and foldable when drawn closed to fit sealingly around the portion of the user's body; an elongate, elastic strip extending through the hem to draw closed sealingly the hem against the portion of the user's body, the elastic strip elastically contracting and tapering when stretched; and, a releasable engagement system operable with a single hand to permit the strip to be stretched, tapered and drawn through the engagement system, to slide the engagement system along the strip to a position adjacent the portion of the user's body, to lock a portion of the stretched, tapered strip in the engagement system to prevent the strip from sliding through the engagement system, and to release the stretched strip to bunch against the engagement system to interfere with slidable passage of the strip through the engagement system.

In still another embodiment of the invention, an improved method is provided for producing a water-resistant unit. The method includes the steps of providing a water-resistant sleeve shaped and dimensioned to fit over a portion of the body of a user. The sleeve includes a distal end, and a proximate end. The sleeve provides an elongate pliable stretchable strand including an elongate elastic inner core, and a sheathing around the core. The core and sheathing take on a flatter configuration when the strand is stretched and drawn around the portion of the body of a user. The method also includes the steps of forming at least one hole through the proximate end of the sleeve; folding the proximate end to form a hem circumscribing the proximate end; inserting an insulator in the proximate end; heat sealing the hem; and, inserting the elongate pliable strand through the hole to circumscribe the proximate end in the hem.

In still a further embodiment of the invention, an improved water-resistant sleeve is provided shaped and dimensioned to fit over a portion of the body of a user. The sleeve includes a distal end; a proximate end; a pliable hem extending substantially continuously around the proximate end of the sleeve and shaped and dimensioned when drawn closed to fit sealingly around the portion of the body of the user; an elongate pliable strand extending through the hem draw closed sealingly the hem against the portion of the user's body. The elastic strand includes an elongate elastic inner core, and a sheathing around the core. The core and sheathing take on a flatter configuration when the strand is stretched and drawn around the portion of the body of a user. The sleeve also includes releasable engaging structure shaped and dimensioned to permit the strand to be stretched, flattened, and drawn through the engaging structure; slide the engaging structure along the strand to a position adjacent the portion of the user's body, lock a portion of the stretched, flattened strand in the engaging structure to prevent the strand from sliding through the engaging structure, and release the stretched strand to bunch against the engaging structure to interfere with slidable passage of said strand through said engaging structure. The strand can have a width in the range of two millimeters to ten millimeters. The engaging structure can be operable with a single hand to manipulate with the hand the engaging structure and the strand. The sleeve can include an opening which has a cross sectional area and which slidably receives the strand, the opening being adjustable to alter the cross sectional area.

In yet a further embodiment of the invention, an improved method is provided for sealingly mounting a pliable, water-resistant sleeve on a portion of the body of a user. The sleeve is shaped and dimensioned to fit over the portion of body of a user. The sleeve includes a distal end and a proximate end; a pliable hem means in the proximate end of the sleeve and foldable in accordion fashion when drawn closed to fit sealingly around the portion of the body of the user; an elongate, pliable, strechable strand extending freely continuously through the hem substantially completely around the proximate end to draw in sealingly the hem against the portion of the body of the user, the strand taking on a flatter configuration when stretched to increase the area of the strand pressed against the portion of the body of the user; and, a releasable engagement structure. The engagement structure is operable to permit the strand to be flattened and drawn through the engagement structure; slide the engagement structure along the strand to a position adjacent the portion of the user's body; and, lock a portion of the flat strand in the engagement structure to prevent the strand from sliding through the engagement structure. The method includes the steps of mounting the sleeve on the portion of the user's body; and, operating the engagement structure means to stretch, flatten, and draw the strand through the engagement structure, to slide the engagement structure along the flattened strand to a position adjacent the portion of the user's body, and to lock a portion of the flattened strand in the engagement structure to prevent the strand from sliding through the engagement structure.

Turning now to the drawings, which depict the presently preferred embodiments of the invention for the purpose of illustrating the practice thereof and not by way of limitation of the scope of the invention, and in which like reference characters refer to corresponding elements throughout the several views, FIG. 1 illustrates a water resistant sleeve 10 shaped and dimensioned to fit over the lower arm of an individual. Sleeve 10 is presently fabricated from plastic, but can be fabricated from any other waterproof or water resistant material. As used herein, water resistant materials include both waterproof material and material which resist penetration by water. Sleeve 10 includes distal end 41 and proximate end 42. Proximate end 42 is the end closest to the user's body when the sleeve 10 is worn in the desired orientation. Distal end 41 is the end furthest from the user's body when the sleeve 10 is worn in the desired orientation. Distal end 41 need not cover the hand or other distal portion of an extremity. For example, distal end 41 might only extend to the wrist of a user's am and not extend over the hand.

Hem 11 is connected to proximate end 42. Hem 11 can be connected by being integrally formed with end 42, by being stitched to end 42, or by any other desired means. Hem 11 functions to direct and to channel elastic strip 12 around the perimeter of sleeve 10. Hem 11 includes open ends or mouths 16 and 17. In FIG. 1, hem 11 comprises one long continuous channel or "tunnel". As would be appreciated by those of skill in the art, hem 11 can comprises a plurality of spaced apart channels, in the same fashion that belt loops on a pair of pants function as a hem for a belt. Hem 11 comprises a pliable material which can fold like an accordion when strip 12 is pulled out of hem 11 to draw closed the opening in end 42 circumscribed by hem 11.

Although the shape and dimension of strip 12 can vary as desired, strip 12 is preferably flat, like a shoe lace, and has, in its normal unstretched state, a width W1 (FIG. 4) in the range of 3 mm to 10 mm, and a thickness T (FIG. 2) in the range of 0.3 to 2 mm. This relatively flat, narrow configuration is preferred in the practice of the invention. If strip 12 is wider, there is a tendency to compress a user's arm or other extremity over a wider area and to interfere with the user's blood circulation. Likewise, if strip 12 is less wide, there is a tendency for the strip 12 to sink or cut into skin, muscle, or other tissue comprising the user's extremity and to restrict the user's blood circulation. If strip 12 is wider, greater frictional forces are generated which make it more difficult for strip 12 to slide through hem 11. Similarly, if the thickness, T, is too small, strip 12 tends to roll up and cut into the tissue comprising the user's extremity. If the thickness, T, is too great, the it is more difficult to readily stretch strip 12 and to move strip 12 through hem 11.

Strip 12 should, when a tensile force of only three to ten pounds is applied, be able to be stretched from its normal unstretched state to a length which is one and one-half to three times its length in its normal unstretched state.

The use of a relatively narrow, flat, elastic strip 12 which can be stretched with the application of relatively little force is important in the practice of the invention, because when the strip 12 is stretched to press and seal the proximate end 42 against a user's arm or other extremity, strip 12 still readily expands and contracts with and permits movement of the muscle and other tissue adjacent strip 12.

In FIG. 4, strip 12 is shown in its normal, unstretched state and has a width W1. In FIG. 5, strip 12 is stretched because it is pulled in the directions of arrow B and C and subjected to a tensile force in the range of three to ten pounds. When strip 12 is stretched, it contracts and tapers, i.e., its width and thickness become less. Width W1 is greater than width W2.

Figure 7:
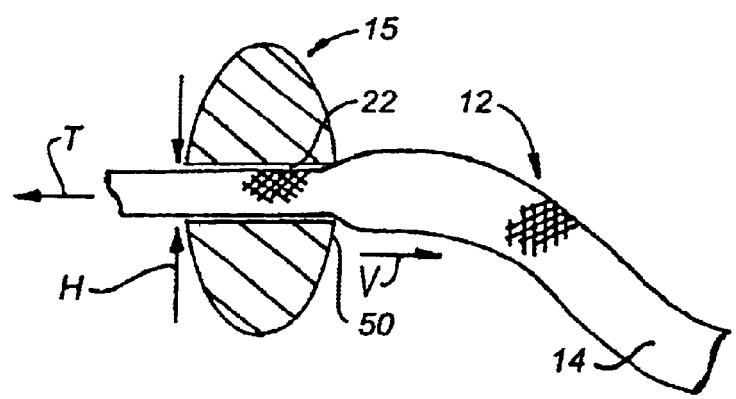
FIG. 7 is a sectional view illustrating the frictional releasable engagement system and the strip of FIG. 2 illustrating the mode of operation thereof.

The characteristics of strip 12 discussed above facilitate the one-handed operation of the engagement system 15 illustrated in FIGS. 2, 3, and 7.

The shape and dimension of engagement system 15 can vary as desired. As would be appreciated by those of skill in the art, a variety of engagement systems can be constructed to perform the functions of system 15. While the engagement system 15 illustrated in FIGS. 2, 3, 7 is unitary, system 15 can include two or more parts, some of which may move with respect to other parts in system 15.

System 15 comprises an egg-shaped elastic member having a pair of generally circular apertures 20, 24 extending therethrough. A slot extends between apertures 20, 24. The slot includes opposing sides 21 and 22. An elongate notch 23 formed in side 21 receives and conforms to an elongate tooth 23 (FIG. 3) formed in side 22. When the ends 45, 46 of system 15 are grasped between the thumb and index finger of one hand and are compressed to generate forces F1 and F2, system 15 takes on the generally circular shape 15A depicted in FIG. 3. When system 15 takes on the circular shape of FIG. 3, sides 21 and 22 are displaced away from one another to form an opening or channel which extends completely through system 15. This opening permits strip 12 to be readily pulled and stretched through the opening. After strip 12 is pulled the desired distance through the opening, the compressive forces F1 and F2 are released and system 15 returns to the egg-shaped configuration of FIG. 2. In the configuration of FIG. 2, sides 21 and 22 compress and frictionally engage strip 12. Tooth 25 also compresses strip 12 into notch 23.

As illustrated in FIG. 1, system 15 is mounted on strip 12 such that ends 13 and 14 extend through system 15. In FIG. 1, dashed lines 15A represent system 15 when it has been temporarily compressed into the spherical configuration 15A shown in FIG. 3.

FIG. 7 is a section view of the system 15 of FIG. 2 taken along section lines 7—7 thereof. FIG. 7 illustrates the "bunching" of strip 12 which takes place during utilization of strip 12 and system 15. In use, sleeve 10 is placed on the arm (or other extremity) of a user in the position shown in FIG. 1, system 15 is held between the thumb and index finger on the right or left hand of a user and is compressed to produce forces F1 and F2 and to produce spherical configuration 15A. Ends 13 and 14 are pulled in the direction of arrow S (FIG. 3) through the opening (shown in FIG. 3) formed in system 15. This pulling of ends 13 and 14 can be accomplished with the $3^{rd}$, $4^{th}$, and $5^{th}$ fingers of the same hand which is holding system 15 between the thumb and index finger of the hand. Ends 13 and 14 are pulled in the direction of arrow S a distance sufficient to stretch strip 12 around arm 18 and sealingly compress the proximate end 42 of sleeve 10 against arm 18. System 15 is slid along strip 12 until system 15 is also adjacent arm 18. Forces F1 and F2 are released, i.e., system 15 is no longer compressed between the thumb and index finger. When forces F1 and F2 are released, system 15 returns to the egg-shaped configuration shown in FIG. 2 and sides 21 and 22 frictionally engage and compress strip 12. The portion of strip 12 which extends outwardly away from system 15 in the direction of T in FIG. 7 and around arm 18 is stretched. The portion of each end 13, 14 of strip 12 which extends outwardly away from system 15 and arm 18 in the direction of arrow V in FIG. 7 is not stretched, but is in its normal unstretched state. The stretched portion of strip 12 is trying to pulled the unstretched portion of strip 12 into system 15. But the portions of system 15, namely sides 21 and 22, which frictionally compress and engage strip 12 prevent this from happening. Consequently, the unstretched portion of strip 12 adjacent system 15 tends to "bunch" against side 50 of system 15 in the manner shown in FIG. 7. The bunched portion of strip 12 is wider than the stretched portion. The bunched portion of strip 12 against side 50 tends to stabilize strip 12 in the position shown in FIG. 7 because the "bunching" makes it more difficult for the bunched portion to slide into system 15 between sides 21 and 22. A method of accentuating this phenomenon is to make the height H of sides 21 and 22 less than the width W1 of strip 12 when strip 12 is not stretched. This allows strip 12 to more readily pass through system 15 when strip 12 is stretched and makes it increasingly difficult for the unstretched, bunched portion of strip 12 to slide into system 15 between sides 21 and 22.

System 15 can be shaped and dimensioned so that it can be held and squeezed between the user's teeth to generate the forces F1 and F2 necessary to produce spherical shape 15A. When spherical shape 15A is produced, the user needs only a single hand to pulls the ends 13, 14 of strip 12 through the opening formed in system 15. Consequently, the user can, with the free hand which will not be covered by sleeve 10, pull sleeve 10 over the other hand and arm 18, can use his teeth to generate forces F1 and F2 on system 15 to produce sphere 15A, and can use his free hand to pull strip 12 through the opening in sphere 15A.

System 15 functions to permit a first opening to be formed which facilitates sliding strip 12 through the opening. System 15 also functions to permit a second opening to be formed which prevents or tends to prevent strip 12 from sliding through the second opening. The second opening can be formed by modifying or changing the shape of the first opening.

Sleeve 10 is presently formed from a polymer or other pliable water resistant material which has a thickness in the range of one to eight mils, preferably three to six mils. The material used to fabricate sleeve 10 can vary as desired, as can the shape and dimension of sleeve 10.

As would be appreciated by those of skill in the art, sleeve 10 can also be sized to be installed over and extend around the chest, mid-section, neck, or head of a user's body.

FIG. 8 illustrates another water resistant sleeve 100 shaped and dimensioned to fit over the lower arm of an individual. Sleeve 100 is presently fabricated from plastic, but can be fabricated from any other waterproof or water resistant material. Sleeve 100 includes distal end 141 and proximate end 142. Proximate end 142 is the end closest to the user's body when the sleeve 100 is worn in the desired orientation. Distal end 141 is the end furthest from the user's body when the sleeve 100 is worn in the desired orientation. Distal end 141 need not cover the hand or other distal portion of an extremity. For example, distal end 141 might only extend to the wrist of a user's arm and not extend over the hand.

Hem 111 is formed on proximate end 142. Hem 111 functions to direct and to channel elastic strip 112 freely continuously around the perimeter of sleeve 100. Hem 111 includes openings 116 and 117. As shown in FIG. 12, hem 111 forms one long continuous inner channel 144. Draw string 112 extends through channel 144 around proximate end 142 and out through opening 116. The entire length of draw string 112 that extends through channel 144 is free to slidably move along channel 144. This is important in the practice of the invention. Some prior art units "tack" down or fix part of hem 111 and an intermediate portion of string 112. Such a "tacking" prevents string 112 from freely sliding through channel 144. The free movement of string 112 through channel 144 is important in producing a generally uniform seal around proximate end 142 when string 112 is tightened by drawing ends through an engagement system 15. Hem 11 comprises a pliable material which can fold like an accordion when portions of string 112 are pulled out of hem 111 through opening 116 to draw closed the opening in end 142 circumscribed by hem 111.

Although the shape and dimension and construction of string 112 can vary as desired, in the embodiment of the invention illustrated in FIG. 8, string 112 is preferably cylindrical and has the construction discussed below and illustrated in FIGS. 9 to 11. The flat construction illustrated in FIGS. 2 to 5 has a disadvantage in that it tends to twist inside the hem, preventing a flat surface from continuously pressing against the user's skin when the strip is tightened about the body portion of the user.

In its normal unstretched state, the width or diameter, indicated by arrows V in FIG. 9, of string 112 is in the range of 1 mm to 10 mm. String 112 includes a core 131 fabricated from rubber or some other elastic material, and includes a sheathing 130 woven from nylon, cotton, wool, or some other fabric. The sheathing 130 has the ability to stretch or distend elastically when core 131 is elastically stretched. However, sheathing 130 ordinarily does not have the ability to stretch as much as core 131 can stretch; consequently, sheathing 130 tends to limit the amount core 131 stretches. When string 112 is in its normal unstretched "at rest" configuration, string 112 has the generally cylindrical cross-sectional area illustrated in FIG. 10. When string 112 is elastically stretched in hem 111 around the portion of the user's body in the directions indicated by arrow(s) X and/or W, string 112 flattens and tends to more evenly distribute the compressive force generated by string 112 over a wider area of the user's body. When, however, the string 112 is not being elastically stretched, the cylindrical shape of the string facilitates sliding the string through hem 111. Even if string 112 twists, string 112 still generally retains its cylindrical shape.

Strip 112 should, when a tensile force of only three to ten pounds is applied, be able to be stretched from its normal unstretched state to a length which is one and one-half to five times its length in its normal unstretched state. The use of a cylindrical elastic string or strip 112 which flattens when stretched is important in the practice of the invention, because when the string 112 is stretched to press and seal the proximate end 142 against and about a user's arm or other extremity, string 112 still readily flattens to distribute the compressive force generated by string over a larger area of the user's body.

The characteristics of string 112 discussed above facilitate the one-handed operation of the engagement system 15 illustrated in FIGS. 2, 3, and 7.

System 15 can be mounted on string 112 and operated in the same manner earlier discussed with respect to strip 12.

Sleeve 100 is presently formed from a polymer or other pliable water resistant material which has a thickness in the range of one to eight mils, preferably three to six mils. The material used to fabricate sleeve 100 can vary as desired, as can the shape and dimension of sleeve 100.

Figure 13:
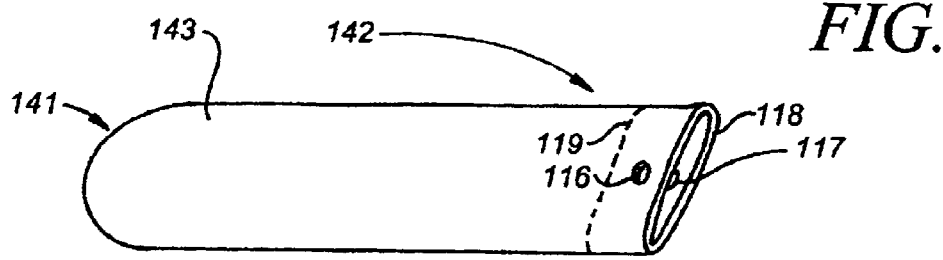
FIG. 13 is a perspective view of a water resistant bag illustrating the method of manufacturing the water resistant covering of the invention.
Figure 14:
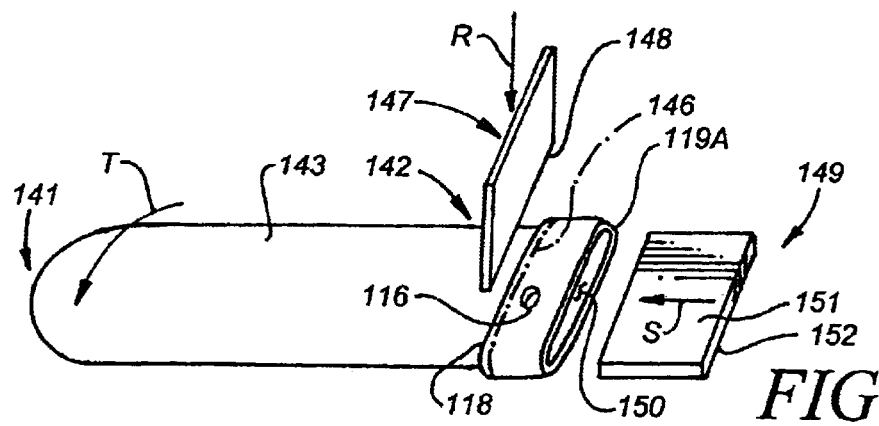
FIG. 14 is a perspective view further illustrating the method of manufacturing the water resistant covering of the invention; and, FIG. 15 is a perspective view further illustrating the method of the invention.
Figure 15:
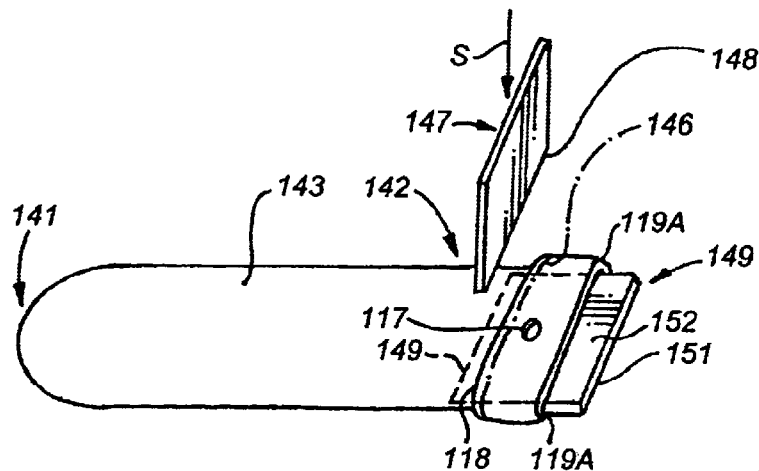

A method for fabricating sleeve 100 is illustrated in FIGS. 13 to 15. In FIG. 13 a plastic bag 143 includes distal end 141 and proximate end 142. Bag 143 is placed in the flattened orientation illustrated in FIG. 13. A punch, die cutter, or other cutting tool is used to cut through bag 143 to form openings 116 and 117. If desired, only a single opening 116 (or 117) can be formed in bag 143. Openings 116, 117 can be cut individually or simultaneously. When openings 116, 117 are cut simultaneously, the cutting tool pierces one side of end 142 to cut opening 116 and continues through the other side of end 142 to cut opening 117 immediately beneath and in registration with opening 116.

A portion of end 142 is folded along fold line 119 to the position illustrated in FIG. 14. A piece of cardboard 149 or other heat insulation material is inserted in opening 150 to the position shown in FIG. 15. A heated plate 147 is displaced in the direction of arrow R until the lower edge 148 contacts the folded plastic along the seal line indicated by reference character 146 and melts or softens the plastic to seal the folded plastic to the underlying portion of bag 143 along line 146 to form about one-half of hem 111. Piece 149 includes top 151 and bottom 152.

Bag 143 is turned over in the direction indicated by arrow T in FIG. 14 to the position shown in FIG. 15, and heated plate 147 is displaced in the direction indicated by arrow S to press lower edge 148 against the folded plastic along seal line 146 in FIG. 15 to soften or melt the plastic along line 146 to complete the formation of sealed hem 111. If desired, the folded plastic can be sealed along seal line 146 using a laser, microwave, or other sealing mechanism. The seal can be formed along the entire line 146 simultaneously by contacting the entire seal line simultaneously with a heating element or other sealing means. String 112 is threaded through hem 111 in the manner illustrated in FIG. 8.

Having described my invention in such terms as to enable those of skill in the art to make and practice it, and having described the presently preferred embodiments thereof, I claim:

1. A method for producing a water-resistant unit, comprising the steps of
   (a) providing a water-resistant sleeve shaped and dimensioned to fit over a portion of the body of a user and including
      (i) a distal end, and
      (ii) a proximate end;
   (b) providing an elongate pliable stretchable strand including
      (i) an elongate elastic inner core, and
      (ii) a sheathing around said core, said core and sheathing taking on a flatter configuration when said strand is stretched and drawn around said portion of the body of a user;
   (c) forming at least one hole through said proximate end of said sleeve;
   (d) folding said proximate end to form a hem circumscribing said proximate end;
   (e) inserting an insulator in said proximate end;
   (f) heat sealing said hem; and,
   (g) inserting said elongate pliable strand through said hole to circumscribe said proximate end in said hem.

2. A water-resistant sleeve shaped and dimensioned to fit over a portion of the body of a user and including
   (a) a distal end;
   (b) a proximate end;
   (c) pliable hem means extending substantially continuously around said proximate end of the sleeve and shaped and dimensioned when drawn closed to fit sealingly around the portion of the body of the user;
   (d) an elongate pliable strand extending through said hem means to draw closed sealingly said hem means against the portion of the user's body, said elastic strand including
      (i) an elongate elastic inner core, and
      (ii) a sheathing around said core, said core and sheathing taking on a flatter configuration when said strand is stretched and drawn around said portion of the body of a user;
   e) releasable engaging means shaped and dimensioned to
      (i) permit said strand to be stretched, flattened, and drawn through said engaging means,
      (ii) slide said engaging means along said strand to a position adjacent the portion of the user's body,
      (iii) lock a portion of said stretched, flattened strand in said engaging means to prevent said strand from sliding through said engaging means, and
      (iv) release said stretched strand to bunch against said engaging means to interfere with slidable passage of said strand through said engaging means.

3. The sleeve of claim 2 wherein said strand has a width in the range of two millimeters to ten millimeters.

4. The sleeve of claim 3 wherein said releasable engaging means is operable with a single hand to manipulate with said hand said engaging means and said strand to accomplish the operations set forth in (e)(i), (e)(ii), (e)(iii), and (e)(iv).

5. The sleeve of claim 4 including an opening which has a cross sectional area and which slidably receives said strand, said opening being adjustable to alter said cross sectional area.

6. A method for sealingly mounting a pliable, water-resistant sleeve on a portion of the body of a user, the sleeve being shaped and dimensioned to fit over the portion of body of a user and including
   a distal end and a proximate end;
   pliable hem means in the proximate end of the sleeve and foldable in accordion fashion when drawn closed to fit sealingly around the portion of the body of the user;
   an elongate, pliable, strechable strand extending freely continuously through the hem means substantially completely around the proximate end to draw in sealingly the hem means against the portion of the body of the user, the strand taking on a flatter configuration when stretched to increase the area of the strand pressed against the portion of the body of the user;
   releasable engaging means operable to
      permit the strand to be flattened and drawn through said engaging means,
      slide the engaging means along the strand to a position adjacent the portion of the user's body, and
      lock a portion of the flat strand in the engaging means to prevent the strand from sliding through the engaging means, said method including the steps of
   (a) mounting the sleeve on the portion of the user's body; and,
   (b) operating the engaging means to
      (i) stretch, flatten, and draw the strand through the engaging means,
      (ii) slide the engaging means along the flattened strand to a position adjacent the portion of the user's body, and
      (iii) lock a portion of the flattened strand in the engaging means to prevent the strand from sliding through the engaging means.

* * * * *